(12) United States Patent
Hayashi et al.

(10) Patent No.: US 8,700,498 B2
(45) Date of Patent: Apr. 15, 2014

(54) FEATURE ANALYZING APPARATUS FOR A SURFACE OF AN OBJECT

(75) Inventors: Yoshinori Hayashi, Yokohama (JP); Hiroshi Wakaba, Yokohama (JP); Koichi Miyazono, Yokohama (JP); Yoko Ono, Yokohama (JP); Hideki Mori, Yokohama (JP)

(73) Assignee: Shibaura Mechatronics Corporation, Yokohama-shi (JP)

( * ) Notice: Subject to any disclaimer, the term of this patent is extended or adjusted under 35 U.S.C. 154(b) by 767 days.

(21) Appl. No.: 12/745,384

(22) PCT Filed: Dec. 1, 2008

(86) PCT No.: PCT/JP2008/071784
§ 371 (c)(1),
(2), (4) Date: Jul. 8, 2010

(87) PCT Pub. No.: WO2009/072458
PCT Pub. Date: Jun. 11, 2009

(65) Prior Publication Data
US 2010/0310150 A1 Dec. 9, 2010

(30) Foreign Application Priority Data
Dec. 5, 2007 (JP) .................................. 2007-314088

(51) Int. Cl.
*G06Q 10/00* (2012.01)
(52) U.S. Cl.
USPC ............................................ 705/28; 382/145

(58) Field of Classification Search
USPC ............................................. 705/28; 382/145
See application file for complete search history.

(56) References Cited

U.S. PATENT DOCUMENTS

| | | | |
|---|---|---|---|
| 5,950,181 A * | 9/1999 | Federl | 706/15 |
| 2006/0152579 A1* | 7/2006 | Utsugi et al. | 348/51 |

FOREIGN PATENT DOCUMENTS

JP 2001-256480 9/2001

* cited by examiner

*Primary Examiner* — Ramsey Refai
(74) *Attorney, Agent, or Firm* — Kratz, Quintos & Hanson, LLP

(57) ABSTRACT

A feature analysis apparatus which enables visual confirmation of features of an inspected object and which enables limitations on the degree of freedom of classification based on the features to made relatively smaller is provided. It acquires inspected object information of an inspected object (S1), analyzes the inspection information to determine values of feature parameters of each of the plurality of layers (S2 to S5), uses values of the plurality of feature parameters and their corresponding directions for each of the plurality of layers to generate a single parameter vector (S2 to S5), converts the parameter vector to a layer vector which is a 3D vector in a predetermined (S2 to S5), and couples the plurality of layer vectors obtained for the plurality of layers in the order of the layers and generates a set of coordinate values of the plurality of nodes obtained in the 3D space as feature information of the inspected object (S6).

12 Claims, 18 Drawing Sheets

FIG.3

| LAYER | FEATURE PARAMETERS | VALUE |
|---|---|---|
| FIRST CONDITION LAYER<br><br>COLOR CHARACTERISTIC TYPE FEATURE QUANTITIES | p1<br>P2<br><br>ph | RED->VIOLET<br>RGB<br>HSV |
| SECOND CONDITION LAYER<br><br>FREQUENCY CHARACTERISTIC TYPE FEATURE QUANTITIES | p1<br>P2<br><br>pi | FFT (2D) |
| THIRD CONDITION LAYER<br><br>HISTOGRAM TYPE FEATURE QUANTITIES | p1<br>P2<br><br>pj | HISTOGRAM |
| FOURTH CONDITION LAYER<br><br>UNIT QUANTITY TYPE FEATURE QUANTITIES | p1<br>P2<br><br>pk | DOTTED LINE SURFACE (SHAPE)<br>LUMINANCE<br>PIXEL DENSITY<br>SIZE (AREA, LENGTH)<br>X-Y COORDINATES |

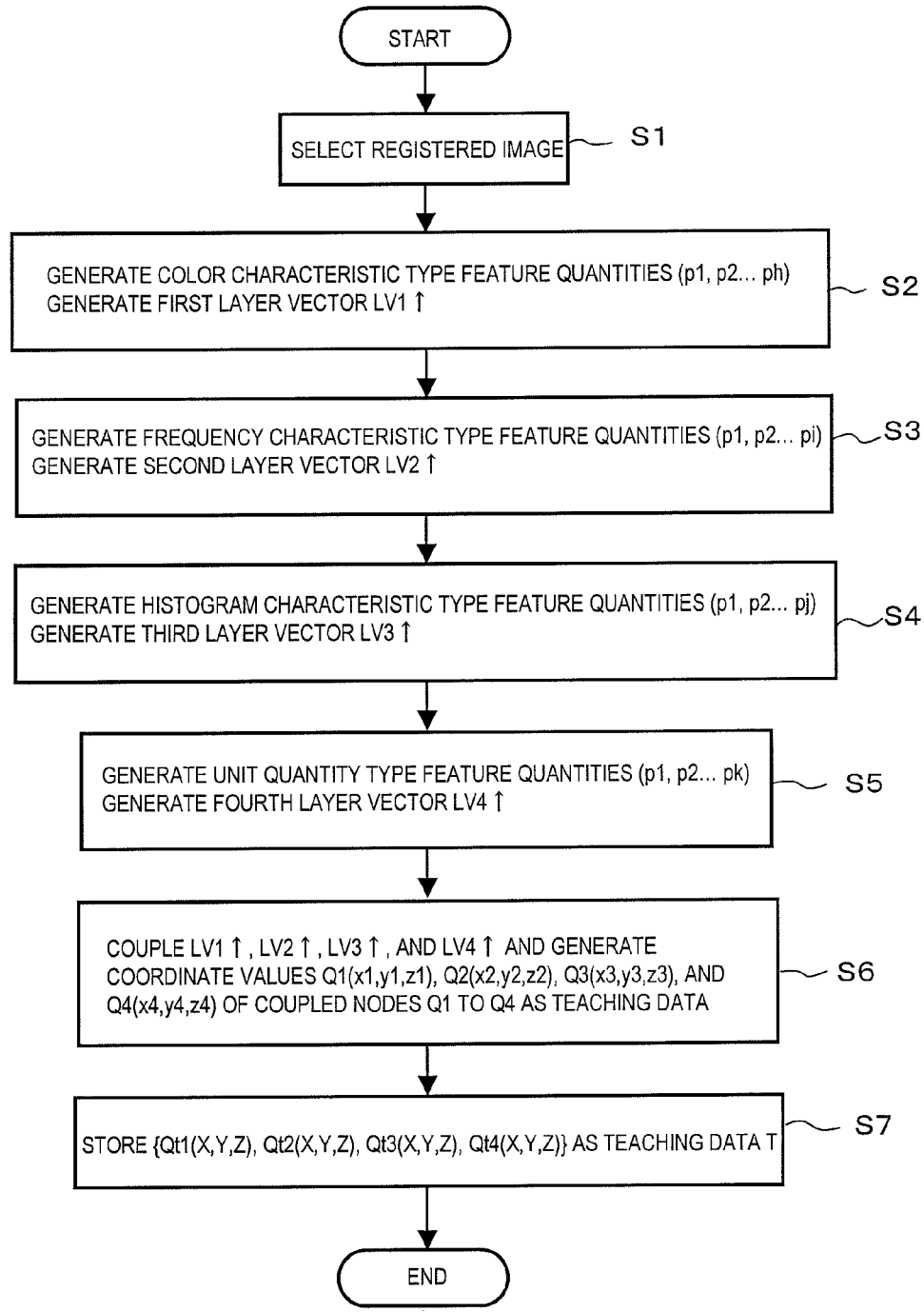

FIG.11

| | CB1 | CB2 | | A | B | C | D |
|---|---|---|---|---|---|---|---|
| Qn1 | $(x_{1a}, y_{1a}, z_{1a})$ | $(x_{1b}, y_{1b}, z_{1b})$ | $f_1$ | $>F_1$ | $<F_1$ | $<F_1$ | $>F_1$ |
| Qn2 | $(x_{2a}, y_{2a}, z_{2a})$ | $(x_{2b}, y_{2b}, z_{2b})$ | $f_2$ | $>F_2$ | $<F_2$ | $<F_2$ | $>F_2$ |
| Qn3 | $(x_{3a}, y_{3a}, z_{3a})$ | $(x_{3b}, y_{3b}, z_{3b})$ | $f_3$ | $>F_3$ | $<F_3$ | $<F_3$ | $>F_3$ |
| Qn4 | $(x_{4a}, y_{4a}, z_{4a})$ | $(x_{4b}, y_{4b}, z_{4b})$ | $f_4$ | $<F_4$ | $<F_4$ | $>F_4$ | $>F_4$ |

FEATURE ANALYZING APPARATUS FOR A SURFACE OF AN OBJECT

TECHNICAL FIELD

The present invention relates to a feature analysis apparatus which analyzes the features of a captured image or other inspected object when capturing an image of the surface of a semiconductor wafer for inspection.

BACKGROUND ART

In the past, an apparatus which classifies a type of a defect at a semiconductor wafer using an image of the same has been proposed (see Patent Citation 1). This apparatus captures an image of a semiconductor wafer (object under inspection), analyzes the obtained image, and classifies the defect etc. of the semiconductor wafer appearing in that image. Specifically, it converts a plurality of parameters expressing the shape, color, image luminance, and other features of a defect appearing in the image into numerical values to generate a vector defined by the set of the plurality of parameters as a feature vector expressing the features of the defect. Further, it classifies a defect included in the image based on the position of a point in a feature space corresponding to that feature vector (feature point).

According to such a feature analysis apparatus, designed to analyze image data expressing an image (inspected object) (inspected object information: for example, luminance values of pixel units) so as to obtain a feature vector expressing the features of the image, it becomes possible for example to classify a defect or other inspected object of a semiconductor wafer based on the feature vector.

Patent Citation 1: Japanese Patent Publication (A) No. 2001-256480

DISCLOSURE OF INVENTION

Technical Problem

However, in the above conventional feature analysis apparatus, if trying to improve the precision of analysis by using a greater number of feature parameters, the feature vector comprised of these greater number of feature parameters becomes a 3D or higher multidimensional vector. For this reason, it is difficult to provide an appropriate user interface enabling visual confirmation of the features of an inspected object or the state of their distribution.

Further, since the features of the inspected object are linked with a single point in the feature space, the degree of freedom of classification ends up being limited.

The present invention was made in consideration of this situation and provides a feature analysis apparatus which enables the easy provision of a user interface enabling visual confirmation of the features of an inspected object and which enables limitations on the degree of freedom of classification based on the features to be made relatively smaller.

Technical Solution

The feature analysis apparatus according to the present invention is configured as an apparatus where a plurality of categories expressing features of an inspected object defined by inspected object information in a predetermined format are set as a plurality of layers, a plurality of feature parameters belonging to each of the plurality of categories are set, and directions on the same plane are assigned to the plurality of respective feature parameters, having a means for acquiring inspected object information of an inspected object under analysis, a parameter value determining means for analyzing the acquired inspected object information and determining values of feature parameters of each of the plurality of layers, a parameter vector generating means for generating a single parameter vector based on values of said plurality of feature parameters and corresponding directions for each of said plurality of layers, a vector converting means for converting the parameter vector obtained for each of the plurality of layers to a layer vector of a 3D vector in a predetermined 3D space, and a feature information generating means for generating a set of coordinate values in said 3D space of a plurality of nodes obtained by coupling a plurality of layer vectors obtained for said plurality of layers in the order of said layers as feature information expressing said features of the inspected object under analysis.

Due to this configuration, the features of an inspected object can be expressed by a set of coordinate points of a plurality of nodes obtained by coupling layer vectors forming 3D vectors, corresponding to the plurality of layers of a 3D space, in the order of the layers.

Further, the feature analysis apparatus according to the present invention can be configured so that. the vector converting means generates the layer vector of a predetermined length with a component of the direction of the parameter vector matching the size of the parameter vector.

Due to this configuration, it is possible to generate a plurality of layer vectors of the same lengths, and the distances between a plurality of nodes obtained by coupling the plurality of layer vectors generated as feature information become constant.

Further, the feature analysis apparatus according to the present invention can be configured further having a feature display controlling means for displaying coupled bodies of nodes and arms corresponding to the coupled plurality of layer vectors on a display unit based on the feature information.

Due to this configuration, it is possible to visually display the features of inspected objects as coupled bodies of nodes and arms.

Furthermore, the feature analysis apparatus according to the present invention can be configured further having a similarity degree generating means for using a positional relationship between nodes specified by respective coordinate values of a set of coordinate values included in first feature information and nodes specified by respective coordinate values of a set of coordinate values included in second feature information so as to generate similarity degree information expressing an extent of similarity of the first feature information and the second feature information.

Due to this configuration, when nodes specified by coordinate values of a set of coordinate values included in first feature information and nodes specified by corresponding coordinate values of a set of coordinate values included in second feature information are displayed in a 3D space, the positional relationship between the group of nodes corresponding to the first feature information and the group of nodes corresponding to the second feature information may be used to judge the extent of similarity of two inspected objects with features expressed by the first feature information and the second feature information.

Further, the feature analysis apparatus according to the present invention can be configured further having a similarity degree information display controlling means for displaying the similarity degree information on the display unit.

Due to this configuration, it is possible to quantitatively determine the extent of similarity of two inspected objects with features expressed by the first feature information and the second feature information.

Further, the feature analysis apparatus according to the present invention can be configured further having a group setting means for holding the feature information as teaching information for each of a plurality of inspected objects and using a state of distribution of teaching information for said plurality of inspected objects to set a plurality of groups into which the inspected objects may be classified.

Due to this configuration, the feature information of actual inspected objects are used as teaching information and the group into which an inspected object should be classified is set based on the state of distribution of the teaching information, so classification in accordance with the actual state of features of an inspected object becomes possible.

Further, the feature analysis apparatus according to the present invention can be configured further having a feature registering means for registering feature information of the inspected object as teaching information of a designated group.

Due to this configuration, it becomes possible to register feature information of inspected objects as teaching information in a designated group.

Furthermore, the feature analysis apparatus according to the present invention can be configured further having a means for using a positional relationship between nodes specified by respective coordinate values of a set of coordinate values included in feature information obtained for an inspected object under analysis and nodes specified by corresponding coordinate values of a set of coordinate values included in at least one teaching information included in a group so as to judge whether the inspected object under analysis belongs to the group.

Due to this configuration, it becomes possible to judge an inspected object corresponding to feature information including a set of coordinate values specifying nodes closer than nodes specified by coordinate values of a set of coordinate values included in at least one teaching information included in a group as belonging to the group.

The teaching information may be any single teaching information included in the group or may be a plurality of teaching information. If a plurality of teaching information, the positional relationship with the individual teaching information may be used to judge if the inspected object belongs to the group or the positional relationship with representative teaching information generated from the plurality of teaching information may be used to judge if the inspected object belongs to the group.

Further, the feature analysis apparatus according to the present invention can be configured further having a classification evaluating means for using a range of distribution of nodes specified by coordinate values of sets of coordinate values included in the plurality of teaching information determined as information corresponding to the first group and a range of distribution of nodes specified by coordinate values of sets of coordinate values included in the plurality of teaching information registered as information corresponding to the second group so as to evaluate if a classification of teaching information by the first group and the second group is suitable or not.

Due to this configuration, if the range of distribution of nodes specified by coordinate values of the sets of coordinate values included in the plurality of teaching information determined as information corresponding to the first group and the range of distribution of nodes specified by coordinate values of the sets of coordinate values included in the plurality of teaching information registered as information corresponding to the second group are clearly separated in the 3D space, it is possible to judge that the classification of the teaching information by these first group and second group is suitable.

Furthermore, the feature analysis apparatus according to the present invention can be configured so that the inspected object is at least part of a captured image of a surface of an object whose surface conditions are to be inspected.

Due to this configuration, the features of a defect etc. formed on the surface of a semiconductor wafer can be analyzed based on the captured image.

Further, the feature analysis apparatus according to the present invention can be configured so that the plurality of categories set as said plurality of layers include a category expressing features relating to colors of the image, a category expressing features relating to frequency characteristics of the image, a category expressing features relating to a state of distribution of darkness or luminance of the image, and a category expressing features relating to physical quantities including a shape, size, and brightness of a feature location in the image.

Further, the feature analysis apparatus according to the present invention can be configured so that the category expressing features relating to colors of the image is set as a lowest layer (first layer), the category expressing features relating to frequency characteristics of the image is set as a second layer, the category expressing features relating to a state of distribution of darkness or luminance of the image is set as a third layer, and the category expressing features relating to physical quantities including a shape, size, and brightness of a feature location in the image is set as a fourth layer.

Advantageous Effects

According to the feature analysis apparatus according to the present invention, the features of an inspected object can be expressed by a set of coordinate points of a plurality of nodes obtained by coupling layer vectors forming 3D vectors, corresponding to a plurality of layers of a 3D space, in the order of the layers, so it is possible to easily provide a user interface which enables the features of an inspected object to be visually confirmed. Further, the features of an inspected object are not expressed by a single point in a feature space like in the past, but are expressed as a set of coordinate points of a plurality of nodes in the 3D space, so it is possible to make the limitations on the degree of freedom of classification based on the features relatively smaller.

BRIEF DESCRIPTION OF DRAWINGS

FIG. 3 A view showing categories of a layer structure set in a feature analysis apparatus and feature parameters set corresponding to the categories.

FIG. 5 A flow chart showing the routine of processing relating to feature analysis.

FIG. 11 A view showing a list of positional relationships of two coupled bodies shown in FIG. 10A to FIG. 10D.

Figure 1:
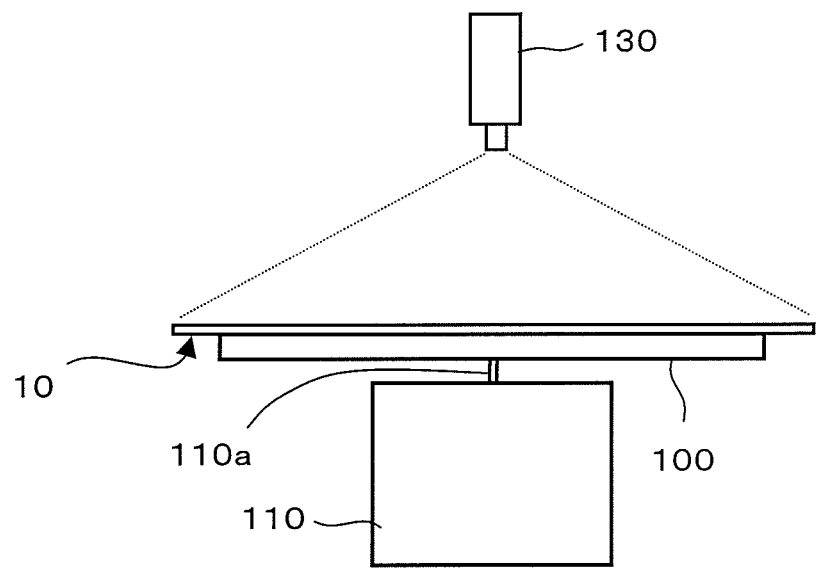
FIG. 1 A view showing a basic configuration of a mechanism of a surface inspection apparatus of a semiconductor wafer to which a feature analysis apparatus according to one embodiment of the present invention is applied.

EXPLANATION OF REFERENCES 10 wafer (semiconductor wafer)
100 stage
110 rotation drive motor
130 camera unit
200 processing unit
210 operating unit
220 display unit
220a, 220b, 220c screen (GUI screen)
221 overall display window
222 designated region display window
223 selected image display window
224 registered defect image display window
225 data display window
226 coupled body display button
227 search button
228 register button
230 defect type input unit
231 selection switch unit
232 suitability condition setting unit
233 first evaluation basis display unit
234 first evaluation display unit
235 second evaluation basis display unit
236 second evaluation display unit
237 parameter display unit
238 update button
239 OK button

BEST MODE FOR CARRYING OUT THE INVENTION

Below, embodiments of the present invention will be explained using the drawings.

An inspection apparatus of a semiconductor wafer to which a feature analysis apparatus of one embodiment of the present invention is applied is configured as shown in FIG. 1.

In FIG. 1, a stage 100 is held at a shaft 110a of a rotation drive motor 110 and can be rotated in one direction. The stage 100 is set with a disk-shaped substrate comprised of a semiconductor wafer (below, simply referred to as a "wafer") 10 in a horizontal state. Note that the stage 100 is set with an alignment mechanism (not shown). The center of the wafer 10 is matched as much as possible with the center of rotation of the stage 100 (axial center of shaft 110a) by suitably setting the wafer 10 on the stage 100.

At a predetermined position above the approximate center part of Lyle stage 100, a camera unit 130 for capturing an image of the surface of the wafer 10 is set. The camera unit 130 is, for example, comprised of an imaging element (area sensor) and an optical system so as to include approximately the entire region of the surface of the wafer 10 placed on the stationary state stage 100 in the range of its field of capture, captures an image of the surface of the wafer 10, and outputs an image signal. Note that, while not shown, an illumination apparatus is set for emitting light toward the surface of the wafer 10 placed on the stage 100. Further, by making the stage 100 turn by a rotation drive motor 110, the camera unit 130 can capture an image of the surface of the wafer 10 at any rotational position.

Figure 2:
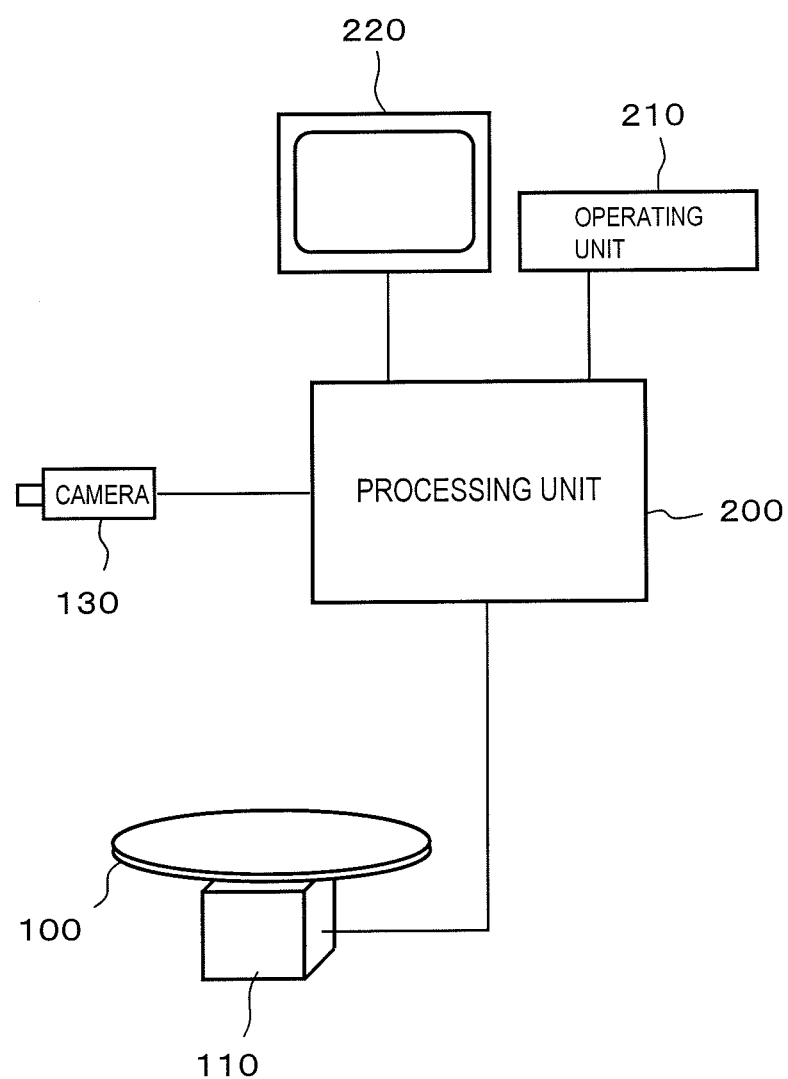
FIG. 2 A block diagram showing a basic configuration of a processing system of a surface inspection apparatus of a semiconductor wafer to which a feature analysis apparatus according to one embodiment of the present invention is applied.

The processing system of the inspection apparatus having the mechanism of the above-mentioned configuration is configured as shown in FIG. 2.

In FIG. 2, the image signal of the camera unit 130 is input to a processing unit 200. The processing unit 200, in accordance with a predetermined operation signal from an operating unit 210, controls the drive operation of the rotation drive motor 110 so as to make the stage 100 rotate and processes the image signal from the camera unit 130 as explained later. Further, the processing unit 200 can display information obtained in the process of this processing on a display unit 220.

This inspection apparatus includes a feature analysis apparatus for analyzing a captured image (inspected object) obtained by capturing an image of the surface of the wafer 10. This feature analysis apparatus analyzes the features of the captured image from the image data showing the captured image (for example, luminance values of pixel units). That function is realized by the processing unit 200. By analyzing the features of the captured image in this way, it becomes possible to analyze and classify damage, defects, etc. at the surface of the wafer 10 reflected in the captured image.

In this feature analysis apparatus (processing unit 200), a plurality of categories showing features of the captured image shown (defined) by the image data based on the image signal output by the camera unit 130 after imaging (for example, luminance values of pixel units) are set as a plurality of "layers". Specifically, as shown in FIG. 3, the category showing features relating to the colors of an image (color characteristic type feature quantities) is set as a first layer (first condition layer: lowest position), the category showing features relating to the frequency characteristics of an image (frequency characteristic type feature quantities) is set as a second layer (second condition layer), the category showing features relating to the state of distribution of luminance of an image (histogram showing relationship of number of pixels to luminance values) (histogram type feature quantities) is set as a third layer (third condition layer), and the category showing features relating to physical quantities including shapes, sizes, and brightnesses of feature parts in the image (able to be deemed as damage or defects), pixel density, etc. (unit quantity type feature quantities) is set as a fourth layer (fourth condition layer: topmost layer).

Each category (layer) is set with a plurality of feature parameters belonging to the same. Specifically, the first layer (category of color characteristic type feature quantities) is set with a plurality of feature parameters p1 to ph expressing red to violet tint or RGB, HSV, and other color components. The second layer (category of frequency characteristic type feature quantities) is set with a plurality of feature parameters p1 to pi including two-dimensional Fast Fourier transform data of the image etc. The third layer (category of histogram type feature quantities) is set with a plurality of feature parameters p1 to pj expressing the peak values, bottom values, or number of histograms expressing the relationship of the number of pixels with respect to the luminance values and other shape type features of histograms converted to numerical values. Furthermore, the fourth layer (category of unit quantity type feature quantities) is set with a plurality of feature parameters p1 to pk expressing the shapes (points, lines, and surfaces), sizes (area and length), etc. of feature parts in the image (able to be deemed damage or defects).

Figure 4:
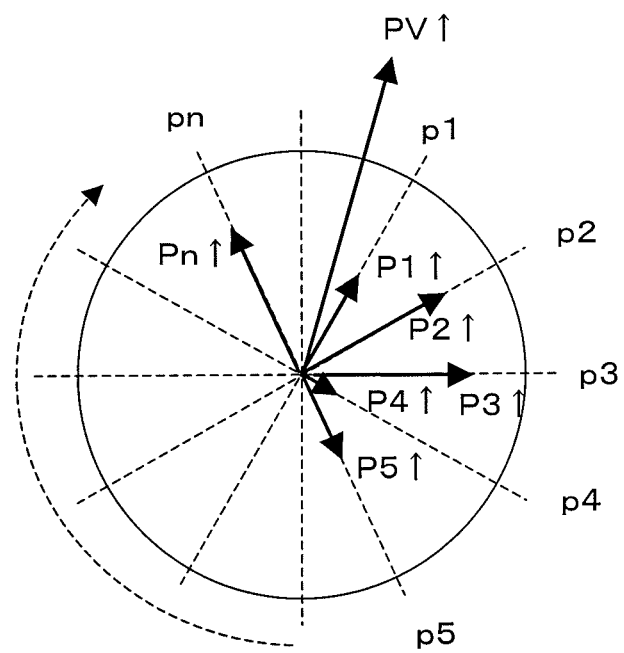
FIG. 4 A view showing a parameter vector PV ↑ generated from the feature parameters p1 to pn.

Furthermore, as shown in FIG. 4, the plurality of feature parameters p1 to pn set at each layer are assigned directions on the same plane. This allocation of directions may be performed by the user operating the operating unit 210.

The feature analysis apparatus built in the processing unit 200 executes processing relating to feature analysis in accordance with the processing shown in FIG. 5. Note that the processing unit 200 extracts and registers images of locations able to be deemed damage or defects (below, referred to as "the images under analysis") from the captured image obtained by capturing an image of the wafer 10. In this state, the processing unit 200 executes the processing relating to the feature analysis.

In FIG. 5, in accordance with an operation by the user at the operating unit 210, the processing unit 200 selects a single image under analysis to be processed from the registered plurality of images under analysis (expressed by luminance values of pixel units) (S1). Further, the processing unit 200 analyzes the selected image for analysis and generates layer vectors corresponding to the different layers (see S2 to S5). Specifically, it determines the feature parameter values at each layer (for example, if the category of color characteristic type feature quantities, the values of the RGB components etc.) and combines the vectors P1 ↑ to Pn ↑ (↑ indicates a vector, same below) defined by those values (magnitudes) and, as shown in FIG. 4, directions set for the feature parameters (for example, vector addition) to generate a single parameter vector PV ↑ (two-dimensional vector).

Figure 6A:
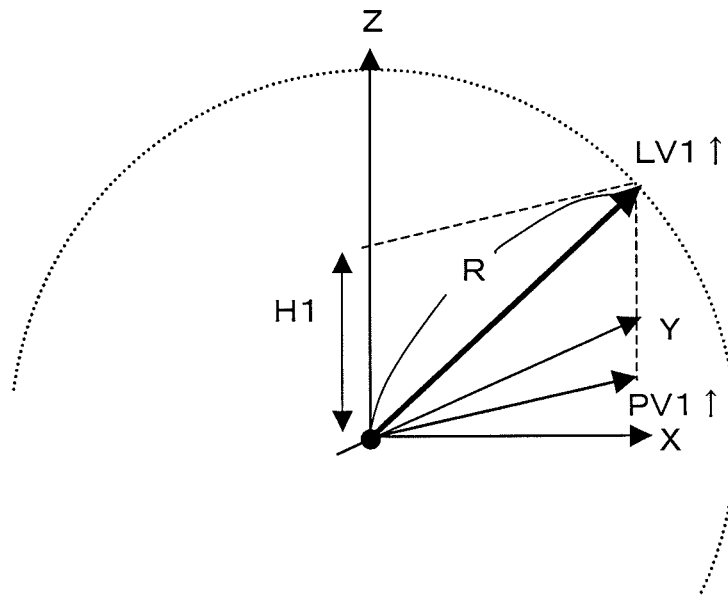
FIG. 6A A view showing a layer vector LV ↑ generated from the parameter vector PV1 ↑.
Figure 6B:
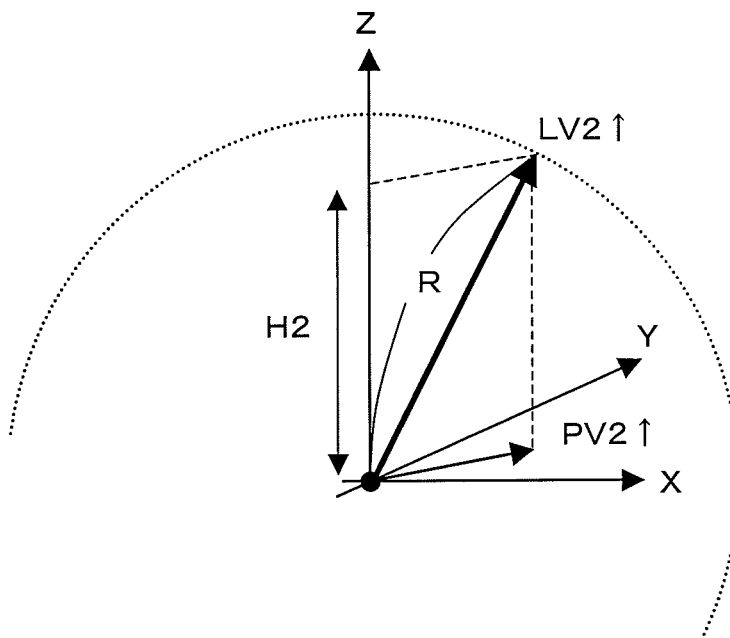
FIG. 6B A view showing a layer vector LV2 ↑ generated from the parameter vector PV2 ↑.

If a single parameter vector PV ↑ is generated for each layer, the 2D vector comprised of the parameter vector PV ↑ is converted to a 3D vector comprised of the layer vector LV ↑ in a 3D space. Specifically, as shown in FIG. 6A and FIG. 6B, layer vectors LV1 ↑ and LV2 ↑ with lengths of a predetermined value R and with components in the directions of the parameter vectors PV1 ↑, PV2 ↑ matching the magnitudes of the parameter vectors PV1 ↑, PV2 ↑ themselves are generated. That is, the layer vector LV ↑ has a length of a constant R. The larger the corresponding parameter vector PV ↑, the smaller the Z-component (see FIG. 6A, FIG. 6B, H1, H2), while the smaller the corresponding parameter vector PV ↑, the larger the Z-component (see FIG. 6A, FIG. 6B, H1, H2).

In this way (S2 to S5), for the first layer, a first layer vector LV1 ↑ based on the first parameter vector PV1 ↑ is generated, for the second layer, a second layer vector LV2 ↑ based on the second parameter vector PV2 ↑ is generated, for the third layer, a third layer vector LV3 ↑ based on the third parameter vector PV3 ↑ is generated, and for the fourth layer, a fourth layer vector LV4 ↑ based on the fourth parameter vector PV4 ↑ is generated.

Figure 7:
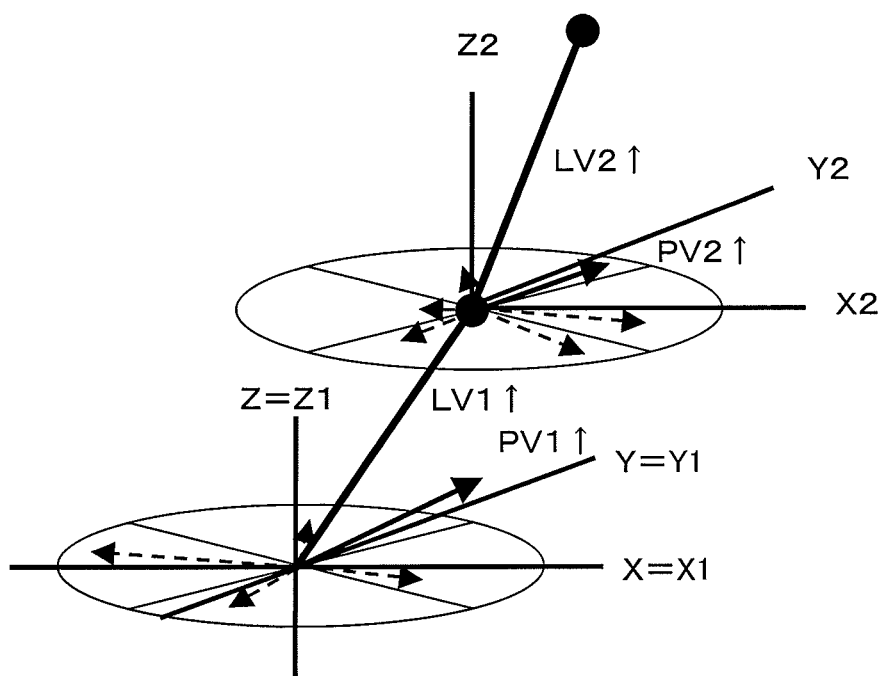
FIG. 7 A view showing the state of coupling of the layer vectors LV1 ↑ and LV2 ↑ for two adjacent layers.
Figure 8:
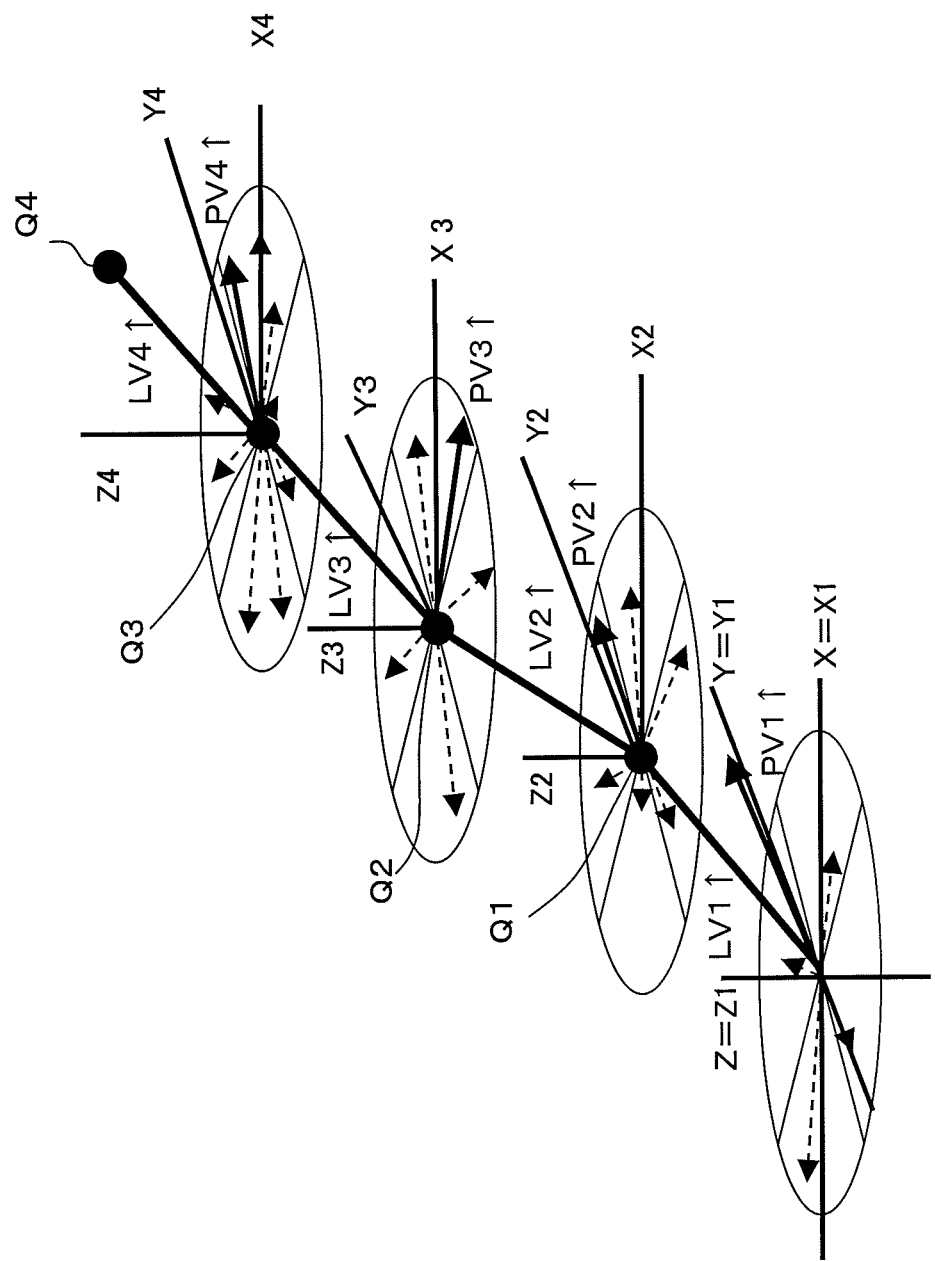
FIG. 8 A view showing the state of coupling of layer vectors LV1 ↑ to LV4 ↑ for four layers.

Next, the processing unit 200 couples the four (plurality of) layer vectors LV1 ↑ to LV4 ↑ obtained for the different layers in the order of the layers to generate coordinate values of coupled nodes Q1 to Q4 in the 3D space as feature data expressing features of the image under analysis (S6). Specifically, first, as shown in FIG. 7, at the front end of the first layer vector LV1 ↑ generated for the first layer, the second layer vector LV2 ↑ generated for the second layer is coupled. Further, as shown in FIG. 8, at the front end of the second layer vector LV2 ↑, the third layer vector LV3 ↑ generated for the third layer is coupled. Furthermore, at the front end of the third layer vector LV3 ↑, the fourth layer vector LV4 ↑ generated for the fourth layer is coupled. The set of the coordinate values (x1,y1,z1), (x2,z2,z2), (x3,y3,y3), and (x4,y4,y4) of a predetermined coordinate system (for example, coordinate system X-Y-Z same as coordinate system X1-Y1-Z1 generating first layer vector LV1) of the nodes Q1, Q2, Q3, and Q4 of the four layer vectors LV1 ↑ to LV4 ↑ coupled in this way is generated as the feature data expressing the features of the image under analysis, that is, the features of a part able to be deemed a defect etc. reflected in the image under analysis.

Figure 9:
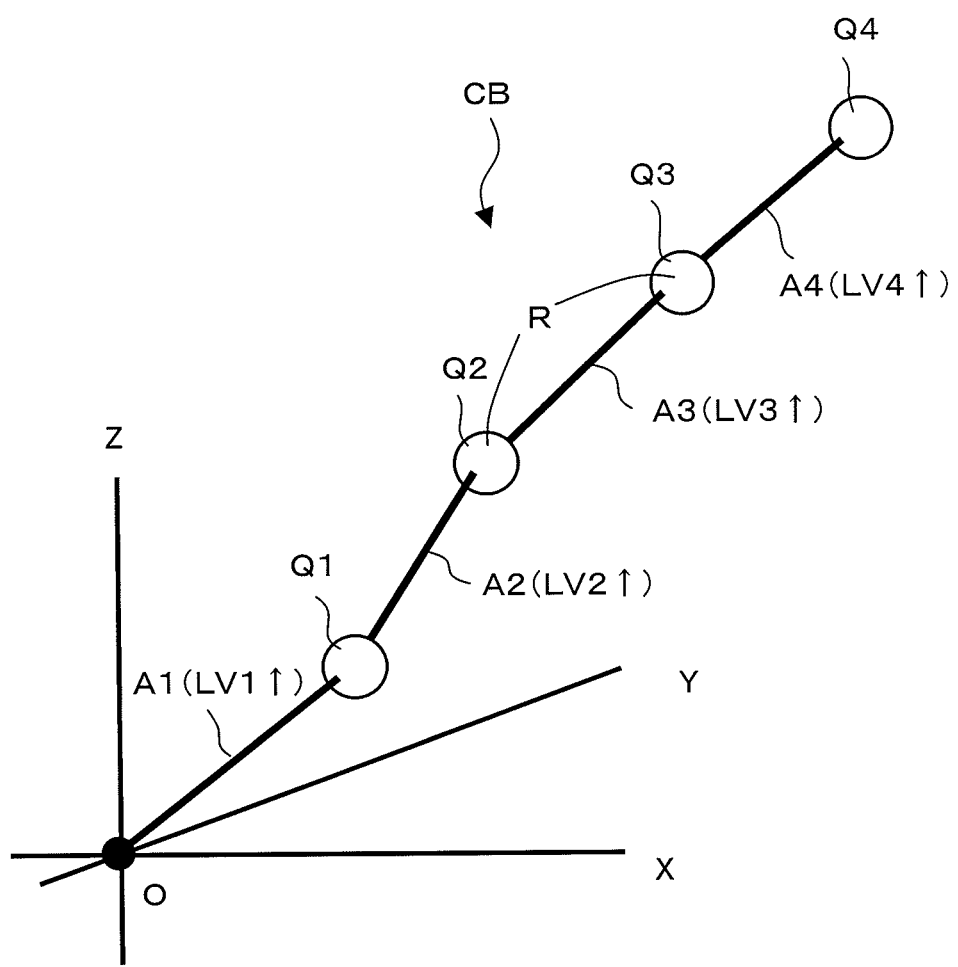
FIG. 9 A view showing a coupled body of nodes and arms obtained by coupling four layer vectors.

The processing unit 200 can use the feature data comprised of the set of coordinate values of the four nodes Q1 to Q4 to display a coupled body CB of the nodes Q1 to Q4 and the fixed length R arms A1 to A4 corresponding to the coupled four layer vectors LV1 ↑ to LV4 ↑ shown in FIG. 9 on the display unit 220. This coupled body CB can be used to visually express the features of the image under analysis (defect part).

Figure 10A:
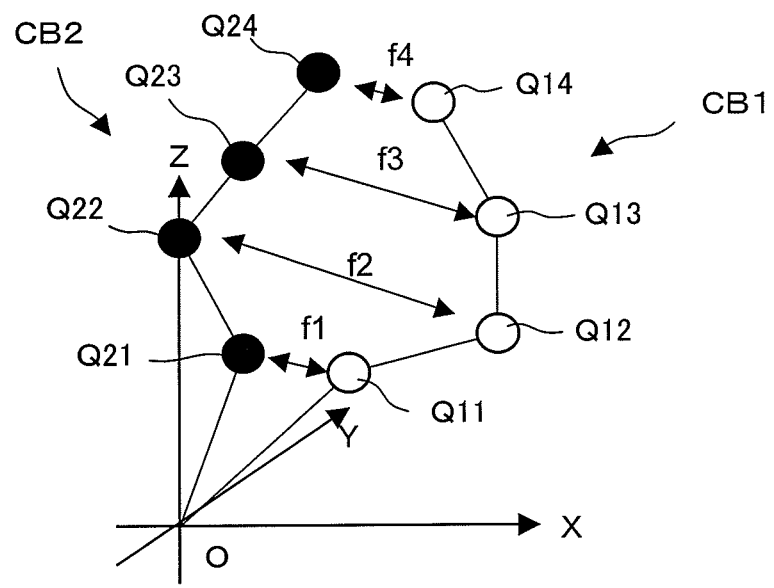
FIG. 10A A view showing a first positional relationship of two coupled bodies expressed by two characteristic data.
Figure 10B:
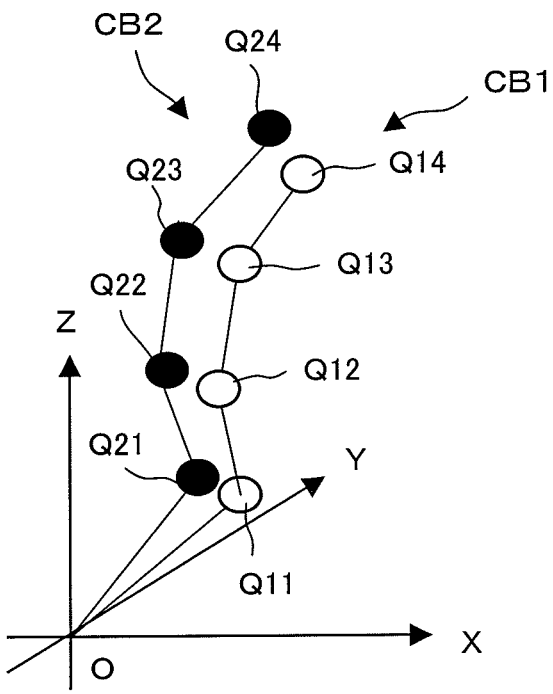
FIG. 10B A view showing a second positional relationship of two coupled bodies expressed by two characteristic data.
Figure 10C:
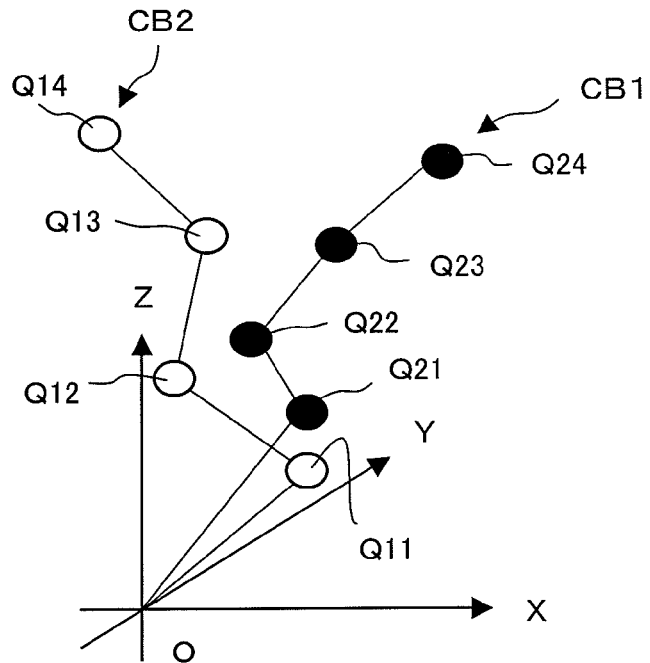
FIG. 10C A view showing a third positional relationship of two coupled bodies expressed by two characteristic data.
Figure 10D:
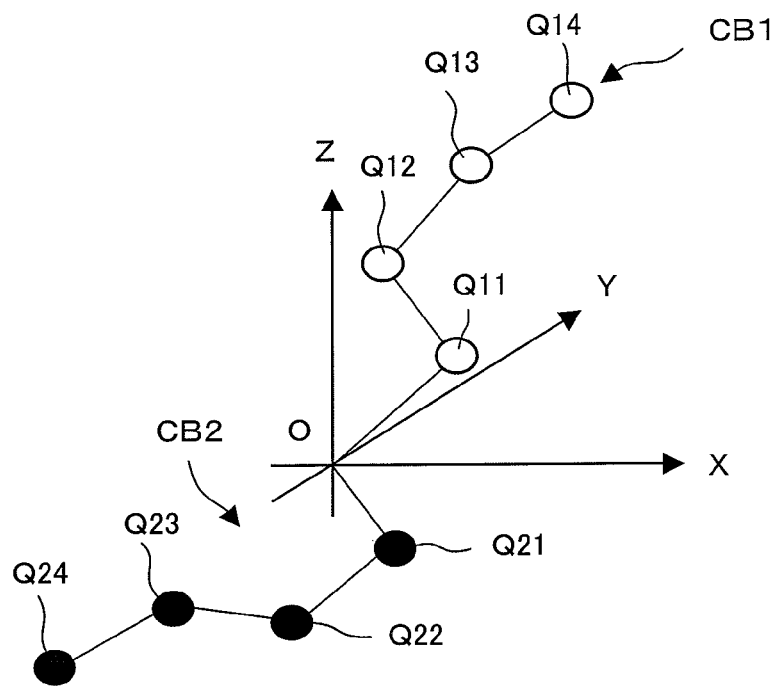
FIG. 10D A view showing a fourth positional relationship of two coupled bodies expressed by two characteristic data.

For example, if two coupled bodies CB1 and CB2 (coupled layer vectors LV1 ↑ to LV4 ↑) obtained for two images under analysis become, for example, as shown in FIG. 10A, FIG. 10B, FIG. 10C, and FIG. 10D, the positional relationships (distances) f1, f2, f3, and f4 of the corresponding node pairs Q11-Q21, Q12-Q22, Q13-Q23, and Q14-Q24 become as shown in FIG. 11. Note that in FIG. 11, $F_1$ to $F_4$ are threshold values for evaluation of the similarity of the two coupled bodies CB1 and CB2 based on the distances of the corresponding node pairs for the different layers. In such a case, the two images under analysis expressed by the coupled bodies CB1 and CB2 in the positional relationship such as shown in FIG. 10B (case of B in FIG. 11) are close in all of the distances of the corresponding node pairs, so can be judged as clearly similar. Further, the two images under analysis expressed by the coupled bodies CB1 and CB2 in the positional relationship such as shown in FIG. 10D (case of D in FIG. 11) are far in all of the distances of the corresponding node pairs, so can be judged to be clearly not similar.

Furthermore, the two images under analysis expressed by the coupled bodies CB1 and CB2 in the positional relationship such as shown in FIG. 10A (case of A in FIG. 11) can be said to be similar if judging the feature parameters of the first layer to the fourth layer (coupled vectors as a whole) overall (front end node Q14 and front end node Q24 are close), but cannot necessarily be said to be similar if judging the first layer to the second layer (positional relationship of node Q12 and node Q22p) and the first layer to the third layer (positional relationship of node Q13 and node Q23) (can be judged similar, but differing in attributes). Further, the two images under analysis expressed by the coupled bodies CB1 and CB2 in the positional relationship such as shown in FIG. 10C (case of C in FIG. 11) conversely cannot be said to be similar if judging the feature parameters of the first layer to the fourth layer overall (front end node Q14 and front end node Q24 are far), but cannot necessarily be said not to be similar if judging the first layer to the second layer (positional relationship of node Q12 and node Q22p) and the first layer to the third layer (positional relationship of node Q13 and node Q23) (can be judged not to be similar, but similar in attributes).

Since the features of an image under analysis are expressed by feature data forming a set of coordinate values of the nodes obtained by coupling the four layer vectors LV1 ↑ to LV4 ↑ forming 3D vectors, as explained above (see FIGS. 10A to 10D and FIG. 11), it becomes possible to use the features for classification with a relatively high degree of freedom.

Note that, in the processing shown in FIG. 5, the obtained feature data {Q1 (x1,y1,z1), Q2 (x2,y2,z2), Q3 (x3,y3,z3), and Q4 (x4,y4,z4)} can be registered by a predetermined operation at the operating unit 210 together with the corresponding image (image under analysis) as teaching data for evaluation of the group of classifications {Qt1 (X,Y,Z), Qt2 (X,Y,Z), Qt3 (X,Y,Z), Qt4 (X,Y,Z)} (S7).

Next, an example of the operation of the above-mentioned feature analysis apparatus will be explained.

Figure 12:
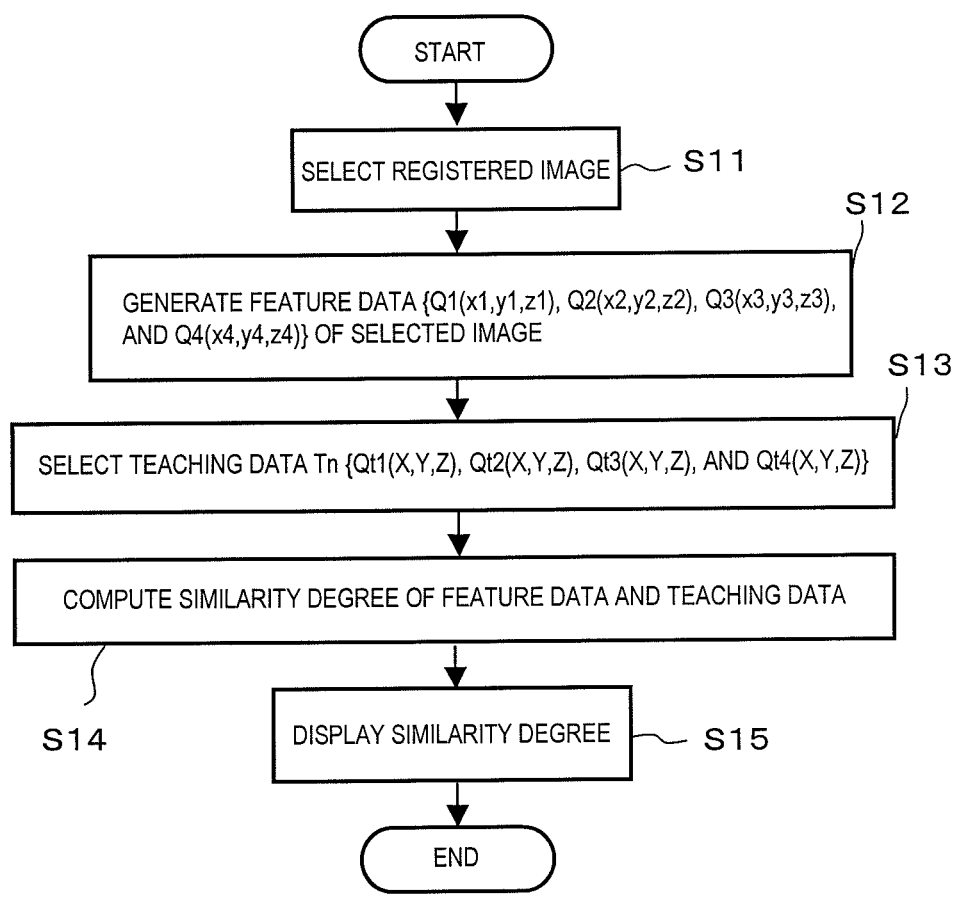
FIG. 12 A flow chart showing a routine of processing for generating a similarity degree.

The processing unit 200 can generate a similarity degree expressing the degree of similarity of two images under analysis in accordance with the routine shown in FIG. 12. In the processing shown in FIG. 12, as the two images under analysis, the two images of a selected registered image and an image forming the basis of teaching data (feature data) are used. That is, the similarity degree of the two images are computed based on the feature data (S11, S12) of the registered image and the teaching data (S13) (S14). The similarity degree is displayed on the display unit 210 (S15).

For example, the feature data {Q1a(x1a,y1a,z1a), Q2a (x2a,y2a,z2a), Q3a(x3a,y3a,z3a), and Q4a(x4a,y4a,z4a)} And {Q1b(x1b,y1b,z1b), Q2b(x2b,y2b,z2b), Q3b(x3b,y3b,z3b), and Q4b(x4b,y4b,z4b)} expressing the features of the two images under analysis are used to compute the similarity degree based on the distances of the corresponding nodes. Specifically, the distances of the nodes are computed according to $$\alpha = \{(xna-xnb)^2 + (yna-ynb)^2 + (zna-znb)^2\}^{1/2}$$

where n is either of 1, 2, 3, or 4
Further, the average value $\alpha_{AVE}$ of the distances between the four sets of nodes is computed as the final similarity degree.

Further, for example, when generating feature data expressing features of an image under analysis, it is possible to use the parameter vectors generated for the different layers (see processing at S2 to S5 of FIG. 5) to generate the similarity degree. Specifically, this can be expressed by the ratio of the distance between end points when joining the starting points of two corresponding parameter vectors at the different layers of two images under analysis and the maximum value of the distance between the end points. The distance between end points becomes the maximum 2R (maximum value) when the sizes of the two corresponding parameter vectors are the predetermined lengths R of the layer vectors and the two corresponding parameter vectors are in opposite directions.

If expressing the corresponding parameter vectors at the different layers as PVna ↑ and PVnb ↑ and defining the components as (pxna,pyna) and (pxnb,pynb), the similarity degree an for the different layers becomes $$\alpha n = 100 - \{\text{distance between end points of two corresponding parameter vectors/maximum value}\}*100 = 100 - [\{(pxna-pxnb)^2 + (pyna-pynb)^2\}^{1/2}/2R]*100$$

This similarity degree αn becomes a value close to 100 if the two corresponding parameter vectors are similar, while becomes a value close to 0 if they are not similar. Further, it is possible to use the average value $\alpha_{AVE}$ of similarity degrees obtained for the different layers as the final similarity degree.

The similarity degree $\alpha_{AVE}$ obtained as explained above can be used as basic information for classification such as classification of images under analysis with high similarity degrees (defects of semiconductor wafer 10 reflected etc.) in the same group.

Further, for example, by selecting an image including a defect of the semiconductor wafer 10 as an image under analysis and linking that image with a type of defect (damage, scratch, etc.), it is possible to classify the feature data (expressed by 3D vectors comprised of four layer vectors) obtained from that image (image under analysis) in accordance with the type of defect of the semiconductor 10. That is, a defect of the semiconductor wafer 10 can be classified in accordance with the feature data. Further, it is possible to specify a defect reflected in the image from the feature data.

Figure 13:
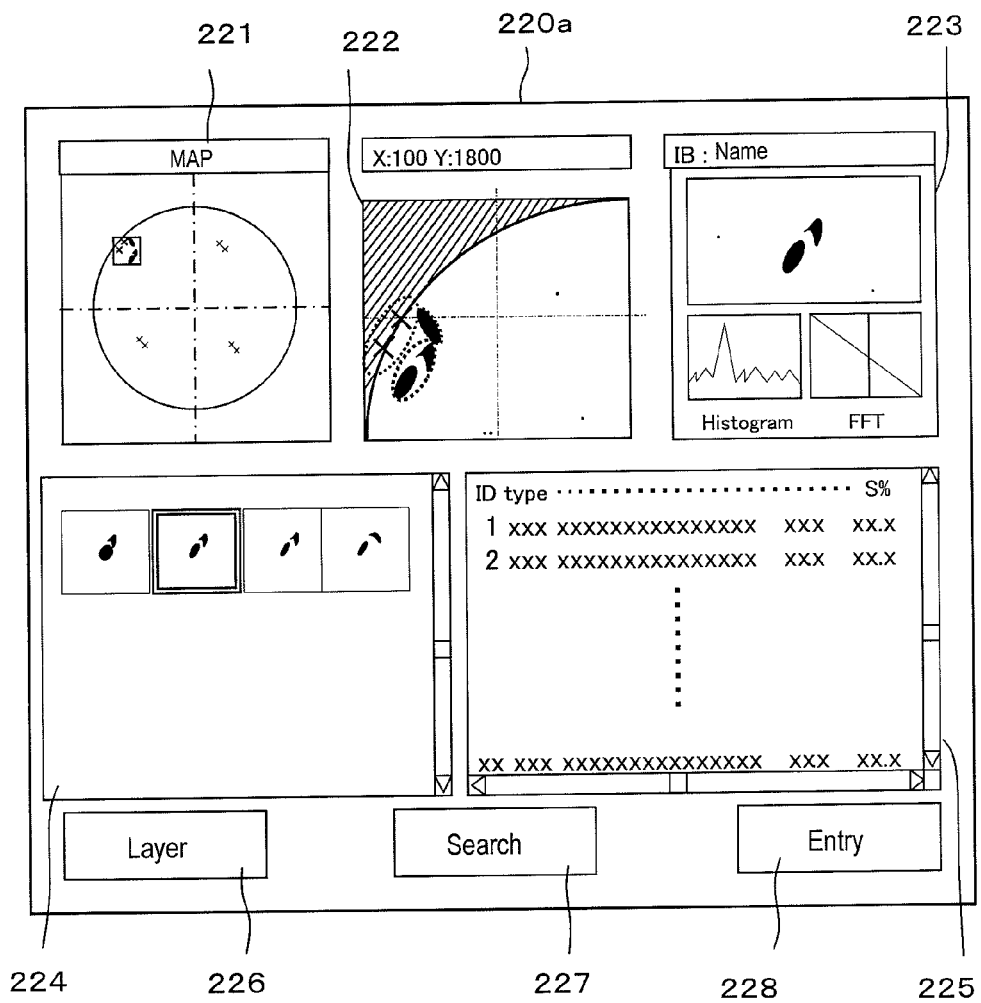
FIG. 13 A view showing an example of a display screen (GUI screen) used as a user interface.

For example, under the control of the processing unit 200, a user interface comprised of a screen 220a (GUI screen) as shown in FIG. 13 is displayed on the display unit 220. This screen 220a has an overall display window 221 which displays the captured semiconductor wafer 10 as a whole, a designated region display window 222 which displays enlarged a rectangular area designated in the overall display window 221 by operation of the operating unit 210, a selected image display window 223 which displays an image selected by operation of the operating unit 210 from the image in the designated region display window 222 and displays feature parameters obtained from that image (histogram of luminance values, frequency characteristics (FFT data), etc.), a registered defect image display window 224 which displays an array of thumbnail images of defect images registered in a designated group, and a data display window 225 which displays various types of data. Note that the selected image display window 223 is provided with a region for inputting the name of a defect (name of classification). Further, the screen 220a has a coupled body display button 226 for displaying the feature data as a coupled body of nodes corresponding to four layers (see FIG. 9), a search button 227 for instructing search processing, and a register button 228 for registering feature data as teaching data.

On such a screen 220a, an image selected as a defect part (damage, scratch, etc.) from a partial image of the semiconductor wafer 10 displayed enlarged in the designated region display window 222 is displayed in the selected image display window 223. If an image of a defect part is selected from the partial image of the semiconductor wafer 10 in this way, the processing unit 200 generates feature data regarding the selected image (see S2 to S6 in FIG. 5) and additionally displays the feature parameters obtained in the process of generation of the feature data (histogram of luminance values, frequency characteristics (FFT data), etc.) in the selected image display window 223.

In this state, if, for example, the search button 227 is operated, the processing unit 200 computes the similarity degree between the feature data regarding the image displayed in the selected image display window 223 and the feature data of a plurality of images already stored as defect images (see FIG.

12) and displays the ID of a defect image (image showing a defect) linked with feature data in a predetermined range of similarity degree with the feature data of the image displayed in the selected image display window 223, together with its similarity degree, in the data display window 225. Due to this, the user can learn that a defect image similar to the selected image, that is, a defect similar to the defect of the semiconductor wafer 10 designated (damage, scratch, etc.), is already stored.

Further, if the register button 228 is operated in the selected image display window 223 in the state with the name of the defect (damage, scratches, etc.) input, the processing unit 200 registers the image displayed in the selected image display window 223 as a defect image of the group specified by the name of defect input and registers the feature data as teaching data of that group. Further, the processing unit 200 displays defect images already registered in the group specified by the name of the defect together with the newly registered defect image (image displayed in selected image display window 223) as thumbnail images in the registered defect image display window 224. Due to this, the user can confirm that the image of the defect selected was registered in the group of similar defect images. Note that, for example, if the operating unit 210 is used to select and delete any of the thumbnail images, the defect image corresponding to the selected thumbnail image and its feature data (teaching data) are removed from the group of defect images (however, defect images and feature data continue being accumulated in the processing unit 200 in a linked state).

Figure 14:
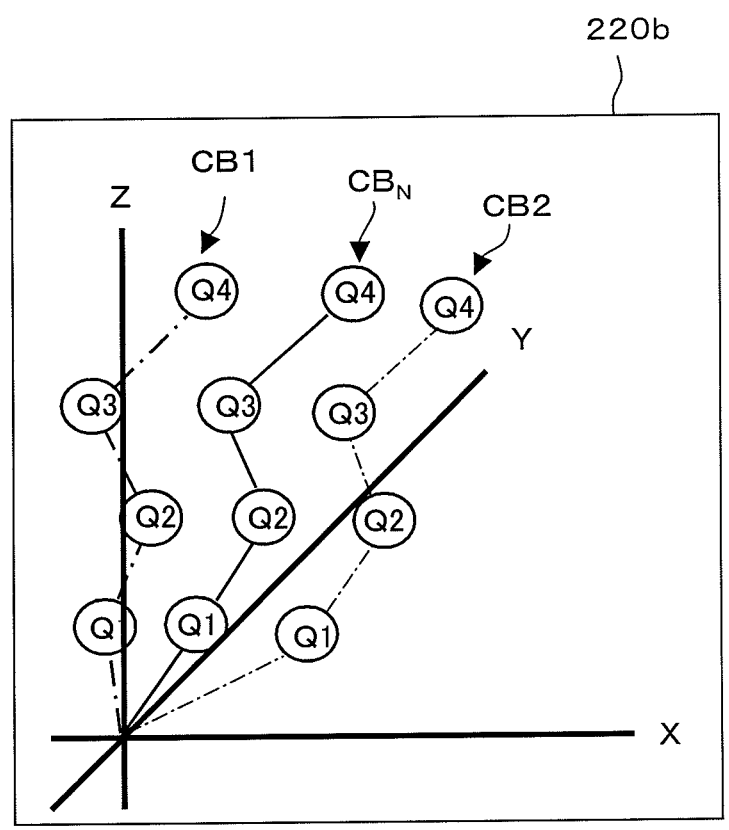
FIG. 14 A view showing an example of a display screen showing feature data as coupled bodies of four layers.

In this state, if the coupled body display button 226 is operated, the processing unit 200 switches the screen 220a shown in FIG. 13 to the screen 220b shown in FIG. 14. Further, the processing unit 200 uses the teaching data registered in the group specified by the name of the defect to display coupled bodies CB of nodes Q1 to Q4 and fixed length R arms corresponding to the coupled four layer vectors LV1 ↑ to LV4 ↑ on the screen 220b. On this screen 220b, the coupled bodies CB1 and CB2 corresponding to the already registered teaching data (for simplification, only two coupled bodies CB1 and CB2 shown) and the coupled body $CB_N$ corresponding to the currently registered teaching data (feature data) are displayed in a visually differentiated state (by color of node, type of arm line, etc.) The user can judged if the current registration of teaching data was suitable or not by the degree of separation or degree of closeness on the screen 220b of the coupled body $CB_N$ corresponding to the currently registered teaching data and the coupled bodies CB1 and CB2 corresponding to the already registered teaching data.

Figure 15:
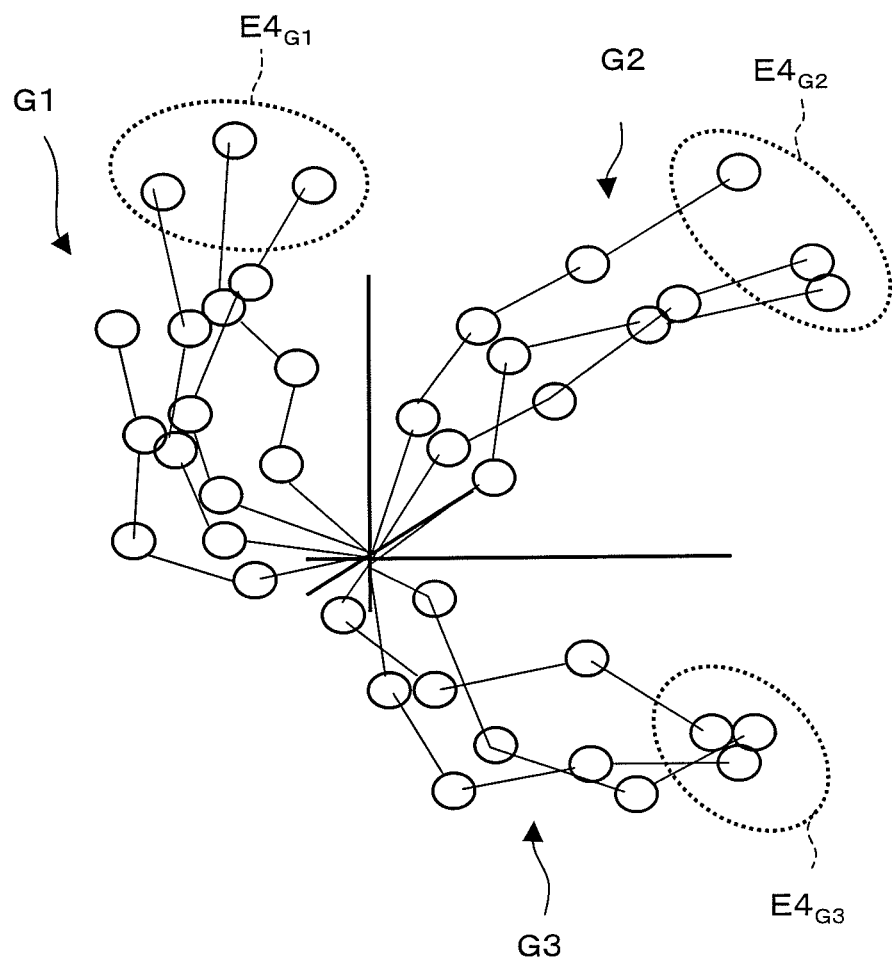
FIG. 15 A view showing the state of teaching data divided into groups.

When the coupled bodies expressing features of a defect image (image under analysis) (feature data and teaching data) are, as shown in FIG. 15, divided into the three groups G1, G2, and G3, it is possible to use the state of the range of distribution of the nodes to evaluate whether the classification of the teaching data (feature data) by two groups is suitable.

Figure 16:
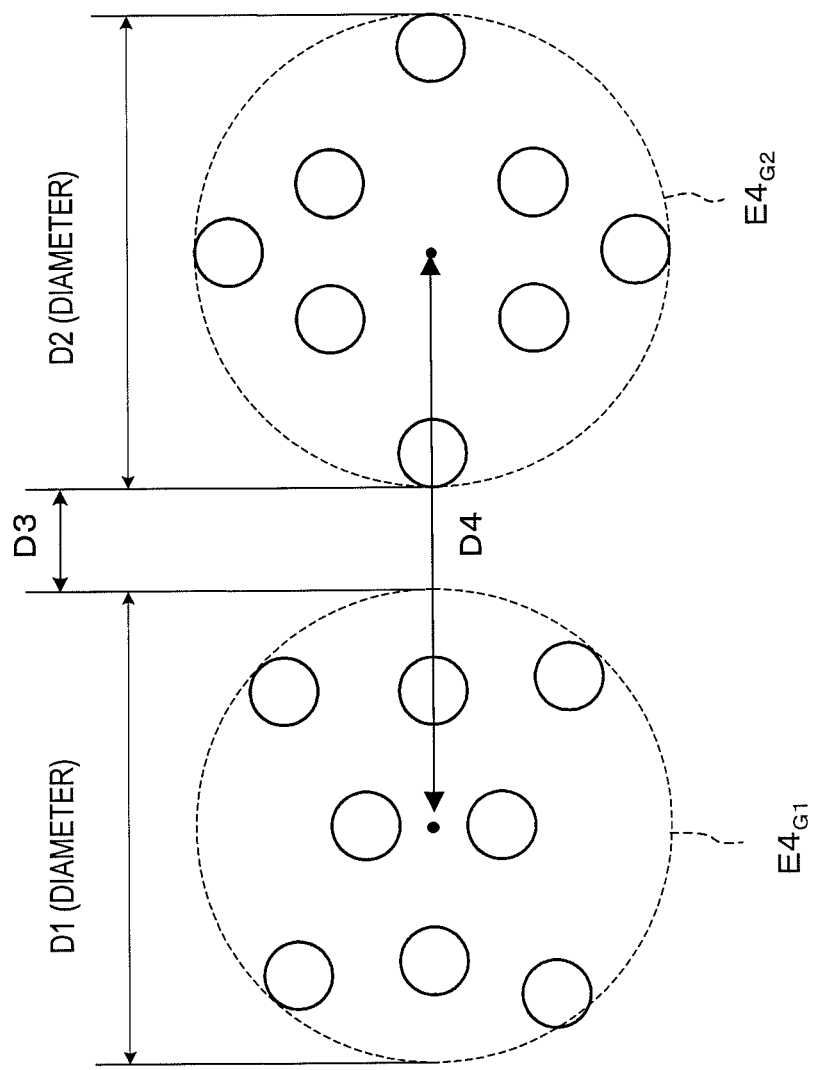
FIG. 16 A view showing the principle of processing for judging if classification of teaching data by groups is suitable.

For example, if looking at the group G1 and the group G2, as shown illustratively in FIG. 16 for the ranges of distribution of nodes (below, referred to as the "node distribution ranges") $E4_{G1}$ and $E4_{G2}$ corresponding to the fourth layer, when it is judged that the node distribution ranges $E4_{G1}$ and $E4_{G2}$ are too close based on the relationship of the distance D4 between center points of the node distribution ranges $E4_{G1}$ and $E4_{G2}$ (for example, spherical ranges), distance D3 between edges of the two node distribution ranges $E4_{G1}$, $E4_{G2}$, and diameters D1 and D2 of the node distribution ranges $E4_{G1}$, $E4_{G2}$, it is possible to evaluate that the classification of the teaching data (feature data) by the two groups is not suitable. On the other hand, when it is judged that the two node distribution ranges $E4_{G1}$ and $E4_{G2}$ are sufficiently separated, it can be evaluated that the classification of teaching data (feature data) by the two groups is suitable.

Figure 17:
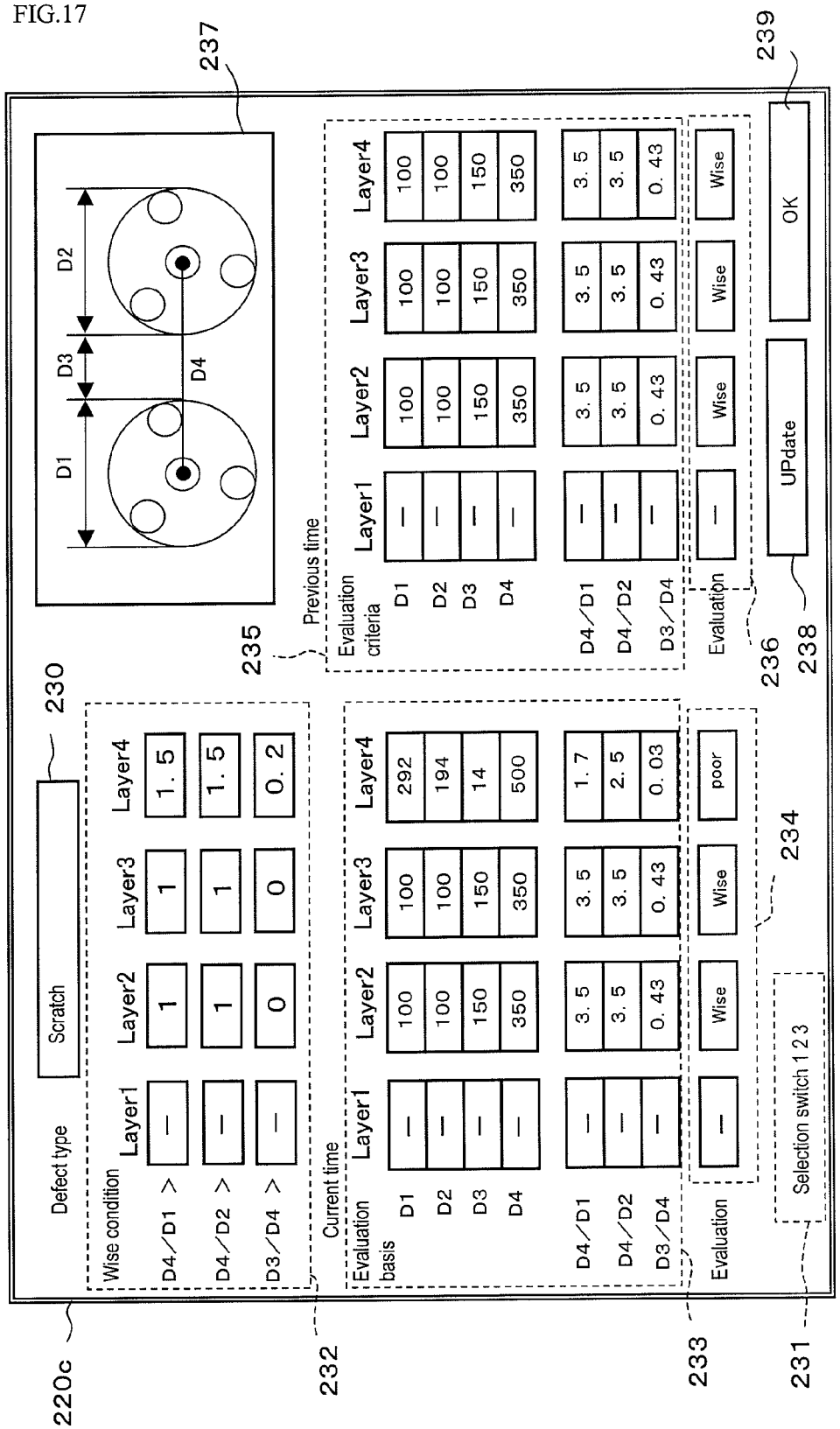
FIG. 17 A view showing an example of a display screen (GUI screen) used as a user interface when judging if classification of teaching data by groups is suitable.

Regarding the evaluation of the classification of the teaching data, the processing unit 200 can display a user interface such as shown in FIG. 17 comprised of a screen 220c (GUI screen) on the display unit 220. This screen 220c has a defect type input unit 230 for inputting the type (name) of defect specifying a group and a selection switch unit 231 for switching and selecting a group for comparison with a group corresponding to the type of defect specified (for example, scratch) (below, referred to as the "designated group") (group under comparison). The numbers "1", "2", and "3" of the selection switch unit 231 show the order of the distance of the groups under comparison in a designated group. If "1" is designated, the group closest to the designated group is selected as the group under comparison. Note that the distance between the two groups may be the average of the distances between the nodes or may be the minimum value or maximum value of the same, Furthermore, it may also be the distance between the front end nodes of the fourth layer in which the features as a whole are reflected.

The screen 220c, furthermore, has a suitability condition setting unit 232, first evaluation basis display unit 233, first evaluation display unit 234, second evaluation basis display unit 235, second evaluation display unit 236, and parameter display unit 237. The parameter display unit 237 displays the parameters necessary for judging if the classification of teaching data by the designated group and group under comparison is suitable (in the same way as the case shown in FIG. 16, the distance D4 between the center points of the two node distribution ranges, the distance D3 between the edges of the two node distribution ranges, and the diameters D1 and D2 of the node distribution ranges). The suitability condition setting unit 232 displays the conditions ("wise" conditions) for the classification of teaching data by the two groups set by the operating unit 210 being suitable. Note that D1 indicates the diameter of a node distribution range of each layer of the coupled body in a designated group, while D2 indicates the diameter of a node distribution range of each layer of the coupled body in a group under comparison.

In this case, regarding second layer (Layer 2) and third layer (Layer 3), $$D4/D1 > 1$$

(when distance D4 between center points of two node distribution ranges is larger than diameter D1 of node distribution range of designated group)

$$D4/D2 > 1$$

(when distance D4 between center points of two node distribution ranges is larger than diameter D2 of node distribution range of group under comparison)

$$D3/D4 > 0$$

(when distance D3 between edges of two node distribution ranges is not "0": two node distribution ranges do not overlap)

Regarding the fourth layer, the conditions of:

$$D4/D1 > 1.5$$

(when distance D4 between center points of two node distribution ranges is greater than 1.5 times diameter D1 of node distribution range of designated group)

$$D4/D2 > 1.5$$

(when distance D4 between center points of two node distribution ranges is greater than 1.5 times diameter D2 of node distribution range of group under comparison)

$$D3/D4 > 0.2$$

(when distance D3 between edges of two node distribution ranges is larger than 20% of distance D4 between center points of two node distribution ranges) are set as conditions for the classification of the teaching data by the two groups being suitable ("wise"). Note that conditions are not set for the first layer.

The first evaluation basis display unit 233 displays the values of the parameters D1, D2, D3, and D4 set for the node distribution ranges of the different layers of the coupled bodies in a designated group and the values of the condition parameters D4/D1, D4/D2, and D3/D4 computed from these for the different layers as basic information for evaluation. Note that, in this case, conditions are not set for the first layer (see suitability condition setting unit 232), so the values of the parameters and condition parameters are not displayed. Further, the first evaluation display unit 234 displays the results of evaluation for the different layers. If suitable, "wise" is displayed, while if not suitable, "poor" is displayed.

The second evaluation basis display unit 235 displays the values of the parameters (D1, D2, D3, and D3) and the values of the condition parameters (D4/D1, D4/D2, and D3/D4) set in the previous evaluation, while the second evaluation display unit 236 displays the previous results of evaluation.

The screen 220c shown in FIG. 17 is, furthermore, formed with an update button 238 for reflecting the currently registered teaching data in the future and an OK button 239 for confirming the content of the suitability condition setting unit 232.

The processing unit 200, when the type of defect is input to the defect type input unit 230, designates the designated group and the group selected by the selection switch unit 231 (default is "1") as the groups under comparison, calculates the values of the diameters D1 of the node distribution ranges of the different layers from all of the teaching data belonging to the designated group and the values of the diameters D2 of the node distribution ranges of the different layers from all of the teaching data belonging to the selected group under comparison, and computes the values of the other parameters D3 and D4 and values of the condition parameters D4/D1, D4/D2, and D3/D4. Further, the processing unit 200 displays these values at the first evaluation basis display unit 233 of the screen 220c. Further, the values of the parameters D1, D2, D3, and D4 obtained the previous time held up to then and the values of the condition parameters D4/D1, D4/D2, and D3/D4 obtained the previous time are transferred to the corresponding regions of the second evaluation basis display unit 235. At this time, the results of evaluation which had been displayed at the first evaluation display unit 234 up to then (suitable ("wise") and unsuitable ("poor")) are also further transferred to the corresponding regions of the second evaluation display unit 236.

In this state, the processing unit 200 compares the values of the condition parameters D4/D1, D4/D2, and D3/D4 displayed at the first evaluation basis display unit 233 and the threshold values showing the conditions set at the suitability condition setting unit 232 and displays suitable ("wise") for layers satisfying the conditions and unsuitable ("poor") for layers not satisfying the conditions at the first evaluation display unit 234. In the example of the screen 220c shown in FIG. 17, at the previous time, the classification of the teaching data by the designated group (type of defect is scratch) and the group under comparison was suitable ("wise") at each layer (see second evaluation display unit 236), but at the current time, the classification of the teaching data by the designated group and the group under comparison at the fourth layer was not suitable ("poor") since the range of distribution of the front end nodes of is too close (D3/D4=0.03<0.2).

For example, as explained above (see FIG. 13), when registering the teaching data, it is possible to judge if the classification of the teaching data by the designated group and the group under comparison to be additionally registered is suitable. When, despite the fact that the result of evaluation before the addition of the teaching data (the previous time) is suitable ("wise"), the result of evaluation after the addition of the teaching data (the current time) is unsuitable ("poor"), it can be judged that the added teaching data is inappropriate as teaching data. Further, when, in the process of successive registration of teaching data, there is a tendency for the result of evaluation to gradually approach unsuitable ("poor") (for region of distribution of nodes to gradually become closer), it can also be judged that the trend in the same type of defects (for example, damage and scratch) is changing. This judgment may be used to check the process of production of the semiconductor wafer 10.

When the result of evaluation is unsuitable ("poor"), it is deemed that the feature parameters (see FIG. 3) and the directions or layers assigned to the feature parameters are unsuitable and it is possible to make them suitable.

Note that, in the screen 220c shown in FIG. 17, if the update button 238 is operated, the current teaching data is set and registered and becomes teaching data relating to classification from the next time on. Further, if the OK button 239 is operated, the values displayed in the suitability condition setting unit 232 are set as the new "wise" conditions, stored in the processing unit 200, and reflected as new display conditions in the first evaluation basis display unit 233 and second evaluation basis display unit 235.

In the above way, in the state where it is judged that the grouping of the teaching data is suitable, the processing unit 200 can use the feature data obtained for an image expressing any defect (defect image) (see processing shown in FIG. 5) and at least one teaching data included in each group to judge the type of the defect. Specifically, the similarity degree of the feature data of a defect image covered and the teaching data included in each group (see processing of FIG. 12) may be computed and the defect judged as one of the group to which the teaching data with the highest similarity degree belongs. Further, the nodes of a coupled body obtained from feature data of a defect image covered can be judged as a defect of a group included in the range of distribution of nodes corresponding to the coupled bodies of the teaching data.

In the above example, a captured image of a semiconductor wafer was explained as the inspected object, but the inspected object is not limited to this. It is also possible to make the captured image of another object the inspected object. Further, so long as something defined by a predetermined format of inspected object information, any object, not just a captured image, can be made the inspected object.

Industrial Applicability

The present invention can easily provide a user interface enabling visual recognition of the features of an inspected object and enables the limits on the degree of freedom of classification based on features to be made relatively smaller, so is useful as a feature analysis apparatus for analyzing the features of a captured image or other inspected object when capturing an image of the surface of a semiconductor wafer for inspection.

The invention claimed is:

1. A feature analysis apparatus where a plurality of categories expressing features of an inspected object defined by inspected object information in a predetermined format are set as a plurality of layers, a plurality of feature parameters belonging to each of the plurality of categories are set, and directions on the same plane are assigned to the plurality of respective feature parameters, having a camera unit for acquiring inspected object information of an inspected object under analysis, a parameter value determining program of a computer processing unit for analyzing the acquired inspected object information and determining values of feature parameters of each of the plurality of layers, a parameter vector generating program of the computer processing unit for generating a single parameter vector based on values of said plurality of feature parameters and corresponding directions for each of said plurality of layers, a vector converting program of the computer processing unit for converting the parameter vector obtained for each of the plurality of layers to a layer vector of a 3D vector in a predetermined 3D space, and a feature information generating program of the computer processing unit for generating a set of coordinate values in said 3D space of a plurality of nodes obtained by coupling a plurality of layer vectors obtained for said plurality of layers in the order of said layers as feature information expressing said features of the inspected object under analysis.

2. A feature analysis apparatus as set forth in claim 1, wherein said vector converting program of the computer processing unit generates the layer vector of a predetermined length with a component of the direction of said parameter vector matching the size of said parameter vector.

3. A feature analysis apparatus as set forth in claim 1, further having a feature display controlling program of the computer processing unit for displaying coupled bodies of nodes and arms corresponding to the coupled plurality of layer vectors on a display unit based on said feature information.

4. A feature analysis apparatus as set forth in claim 1, further having a similarity degree generating program of the computer processing unit for using a positional relationship between nodes specified by respective coordinate values of a set of coordinate values included in first feature information and nodes specified by respective coordinate values of a set of coordinate values included in second feature information so as to generate similarity degree information expressing an extent of similarity of said first feature information and said second feature information.

5. A feature analysis apparatus as set forth in claim 1, further having a similarity degree information display controlling program of the computer processing unit for displaying said similarity degree information on said display unit.

6. A feature analysis apparatus as set forth in claim 1, further having a group setting program of the computer processing unit for holding said feature information as teaching information for each of a plurality of inspected objects and using a state of distribution of teaching information for said plurality of inspected objects to set a plurality of groups into which the inspected objects may be classified.

7. A feature analysis apparatus as set forth in claim 6, further having a feature registering program of the computer processing unit for registering feature information of said inspected object as teaching information of a designated group.

8. A feature analysis apparatus as set forth in claim 6, further having a similarity degree generating program of the computer processing unit for using a positional relationship between nodes specified by respective coordinate values of a set of coordinate values included in feature information obtained for an inspected object under analysis and nodes specified by corresponding coordinate values of a set of coordinate values included in at least one teaching information included in a group so as to judge whether said inspected object under analysis belongs to said group.

9. A feature analysis apparatus as set forth in claim 6, further having a classification evaluating program of the computer processing unit for using a range of distribution of nodes specified by coordinate values of sets of coordinate values included in the plurality of teaching information determined as information corresponding to the first group and a range of distribution of nodes specified by coordinate values of sets of coordinate values included in the plurality of teaching information registered as information corresponding to the second group so as to evaluate if a classification of teaching information by said first group and said second group is suitable or not.

10. A feature analysis apparatus as set forth in claim 1, wherein said inspected object is at least part of a captured image of a surface of an object whose surface conditions are to be inspected.

11. A feature analysis apparatus as set forth in claim 10, wherein the plurality of categories set as said plurality of layers include a category expressing features relating to colors of the image, a category expressing features relating to frequency characteristics of the image, a category expressing features relating to a state of distribution of darkness or luminance of the image, and a category expressing features relating to physical quantities including a shape, size, and brightness of a feature location in the image.

12. A feature analysis apparatus as set forth in claim 11, wherein said category expressing features relating to colors of the image is set as a lowest layer (first layer), said category expressing features relating to frequency characteristics of the image is set as a second layer, said category expressing features relating to a state of distribution of darkness or luminance of the image is set as a third layer, and said category expressing features relating to physical quantities including a shape, size, and brightness of a feature location in the image is set as a fourth layer.

* * * * *